United States Patent
Ishikawa et al.

(10) Patent No.: US 6,478,752 B1
(45) Date of Patent: Nov. 12, 2002

(54) CATHETER GUIDE WIRE AND PRODUCTION METHOD FOR THE SAME

(75) Inventors: Takeshi Ishikawa, Yokohama (JP); Yukihisa Kurebayashi, Yokohama (JP)

(73) Assignee: Piolax Medical Devices, Inc., Kanagawa (JP)

( * ) Notice: Subject to any disclaimer, the term of this patent is extended or adjusted under 35 U.S.C. 154(b) by 0 days.

(21) Appl. No.: 09/857,542

(22) PCT Filed: Dec. 10, 1999

(86) PCT No.: PCT/JP99/06963

§ 371 (c)(1),
(2), (4) Date: Jun. 6, 2001

(87) PCT Pub. No.: WO00/35528

PCT Pub. Date: Jun. 22, 2000

(30) Foreign Application Priority Data

Dec. 11, 1998 (JP) .......................... 10-353520

(51) Int. Cl.⁷ .................................. A61B 5/00
(52) U.S. Cl. ..................................... 600/585
(58) Field of Search .................. 600/434, 435, 600/585; 604/281

(56) References Cited

U.S. PATENT DOCUMENTS 5,069,226 A    12/1991   Yamauchi et al.
5,341,818 A  *  8/1994   Abrams et al. ............. 128/772
5,931,819 A  *  8/1999   Fariabi ........................ 604/281
5,980,471 A  * 11/1999   Jafari .......................... 600/585
6,165,292 A  * 12/2000   Abrams et al. ............. 148/563
6,190,332 B1 *  2/2001   Muni et al. ................. 600/585

FOREIGN PATENT DOCUMENTS

| EP | 901080978 | 10/1990 |
| JP | 2024549 | 7/1988 |
| JP | 2024550 | 7/1988 |
| JP | 324144 | 3/1991 |
| JP | 2587728 | 9/1993 |
| JP | 2557064 | 10/1993 |
| JP | 06026331 | 10/1995 |
| JP | 7275366 | 10/1995 |

* cited by examiner

Primary Examiner—Max Hindenburg
(74) Attorney, Agent, or Firm—Howard & Howard (57) ABSTRACT

In a catheter guide wire 1 formed of an identical material, since the catheter guide wire 1 consists of a portion 7 having a transformation point and portions 3, 5 not having a transformation point, the body portion 3 will not be excessively flexible and has appropriate rigidity while the connect portion 7 maintains flexibility, so that the power of pressing the catheter guide wire 1 is sufficiently transmitted to the connect portion 7 side from the body portion 3 side, whereby insertion operability of the guide wire 1 is improved.

8 Claims, 7 Drawing Sheets

CATHETER GUIDE WIRE AND PRODUCTION METHOD FOR THE SAME

TECHNICAL FIELD

The present invention relates to a catheter guide wire used in inserting a catheter into a blood vessel, ureter, trachea or the like.

BACKGROUND ART

As conventional catheter guide wires, those disclosed in Japanese Patent Application Publication No. 2-24549 and Japanese Patent Application Publication No. 2-24550 are known, which will be briefly explained in the following.

That is, the above-mentioned catheter guide wire is formed of an identical material and comprises a body portion, a tip end portion having a cross section smaller than that of the body portion, and a connect portion for connecting the body portion and the tip portion. Each portion (body portion, tip end portion and connect portion) has a transformation point and the property of super-elasticity (See for definition of the term JIS H7001 published by Japanese Standard Association).

Accordingly, the above-mentioned catheter guide wire can have flexibility (softness) by super-elastically deforming via stress inducible martensite transformation and its reverse transformation. Therefore, it is possible to insert the guide wired into a blood vessel or the like in conformance with the shape of the blood vessel or the like.

Though the prior art enables the catheter guide wire to be inserted in conformance with the shape of a blood vessel or the like because each portion (body portion, tip end portion and connect portion) has the respective flexibility, since the rigidity of the body portion is not sufficient, the power of pressing the catheter guide wire is not sufficiently transmitted from the body portion side to the connect portion side, which leads to the problem of poor insertion operability of the catheter guide wire.

DISCLOSURE OF THE INVENTION

The present invention was made in response to such a requirement. Therefore, it is an object of the invention to provide a catheter guide wire and a method of producing a catheter guide wire which eliminate the above-mentioned problem and drawback.

In order to achieve the above object, a catheter guide wire according to the first aspect of the present invention is a catheter guide wire which comprises a body portion, a tip end portion and a connect portion for connecting the body portion and the tip end portion, and is formed seamlessly of an identical material, the catheter wire being featured in that it consists of a part having a transformation point and a part not having a transformation point, and that the body portion is the part not having a transformation point.

According to the specified feature of the first aspect of the present invention, it is possible to super-elastically deform the part having a transformation point via stress inducible martensite transformation and its reverse transformation, so that it has flexibility (softness). On the other hand, the part not having a transformation point, particularly, the body portion will not super-elastically deform, so that it will not be excessively flexible and has appropriate rigidity.

Therefore, the power of pressing the catheter guide wire is sufficiently transmitted from the body portion side to the connect portion side, which improves the insertion operability of the catheter guide wire.

According to the specified feature of the first aspect of the present invention, a catheter guide wire according to the second aspect of the present invention is characterized in that, the body portion and the tip end portion are the part not having a transformation point, and the connect portion is the part having a transformation point.

According to the specified feature of the second aspect of the present invention, since the connect portion is the part having a transformation point and thus can super-elastically deform via stress inducible martensite transformation and its reverse transformation, it has flexibility. Furthermore, since the body portion is the part not having a transformation point, it will not super-elastically deform, and hence it has appropriate rigidity without becoming excessively flexible. Furthermore, since the tip end portion is the part not having a transformation point, it will not super-elastically deform, but can be plastically deformed.

Therefore, in addition to the effect of the first aspect, it is possible to plastically deform the tip end portion, which enables a physician to shape the tip end portion into an appropriate shape in accordance with the situation during operation.

According to the specified features of the first aspect and the second aspect of the present invention, a catheter guide wire according to the third aspect of the present invention is characterized in that the material is a material based on Ni and Ti; the part not having a transformation point is a part subjected to a heat treatment at a temperature of less than 350° C. after cold working; and the part having a transformation point is a part subjected to a heat treatment at a temperature of more than or equal to 400° C. (preferably 400° C. to 600° C.) after cold working.

According to the specified feature of the third aspect of the present invention, the same operation as that of either the first aspect or the second aspect is achieved.

A catheter guide wire according to the fourth aspect of the present invention is a catheter guide wire which comprises a body portion, a tip end portion and a connect portion for connecting the body portion and the tip end portion, and is seamlessly formed of a material based on Ni and Ti, the catheter guide wire being featured in that a rigidity value of the body portion is larger that of the connect portion.

In this context, the term "rigidity value" represents the degree of strength against bending rather than the degree of strength against tensile.

According to the specified feature of the fourth aspect of the present invention, since the rigidity value of the body portion is larger than that of the connect portion, the body portion will not become excessively flexible but has appropriate rigidity.

Therefore, the power of pressing the catheter guide wire is sufficiently transmitted to the connect portion side from the body portion side, which improves the insertion operability of the catheter guide wire.

According to the specified feature of the fourth aspect of the present invention, the catheter guide wire according to the fifth aspect of the present invention is characterized in that the body portion has a rigidity value of 5,500 to 7,000 Kg/mm$^2$, and the connect portion has a rigidity value of 3,500 to 5,000 Kg/mm$^2$.

Besides the specified feature of the fourth aspect of the present invention, the catheter guide wire according to the sixth aspect of the present invention is characterized in that the body portion has a rigidity value of 6,500 Kg/mm$^2$ or more, and the connect portion has a rigidity value of 5,000 to 6,000 Kg/mm$^2$.

According to the specified features of the fifth and sixth aspects of the invention, the connect portion has flexibility, while the body portion has appropriate rigidity without becoming excessively flexible.

The seventh aspect of the present invention is a method of producing a catheter guide wire which comprises a body portion, a tip end portion and a connect portion for connecting the body portion and the tip end portion, and is seamlessly formed of a material based on Ni and Ti and subjected to a cold working, the method comprising the steps of: subjecting the body portion and the tip end portion to a heat treatment at a temperature of less than 350° C., and subjecting the connect portion to a heat treatment at a temperature of 400° C. or more (preferably 400° C. to 600° C.).

According to the specified feature of the seventh aspect of the present invention, the fact that a transformation point will not occur when the material is subjected to a heat treatment at a temperature of less than 350° C. and that a transformation point will occur when the material is subjected to a heat treatment at a temperature of 400° C. or more (preferably 400° C. to 600° C.) has been experimentally shown. Also the fact that the rigidity value will become large when the material is subjected to a heat treatment at a temperature of less than 350° C. and that super-elastic deformation will occur when the material is subjected to a heat treatment at a temperature of 400° C. or more (preferably 400° C. to 600° C.) has been experimentally shown.

Therefore, the body portion is the part not having a transformation point, so that it will not super-elastically deform and hence has appropriate rigidity without becoming excessively flexible. Similarly, the tip end portion is the part not having a transformation point, so that it will not super-elastically deform and can be plastically deformed. Furthermore, the connect portion is the part having a transformation point, so that it can super-elastically deform via stress inducible martensite transformation and its reverse transformation, and has flexibility.

According to the above-mentioned operation, the power of pressing the catheter guide wire is sufficiently transmitted to the connect portion side from the body portion side, which leads an effect of improving the insertion operability of the catheter guide wire.

Furthermore, since it is possible to plastically deform the tip end portion, a physician can shape the tip end portion into an appropriate shape in accordance with the situation during operation.

According to the specified feature of the seventh aspect of the present invention, the eighth aspect of the present invention is characterized in that working rate of the cool working is 50% or more.

According to the specified feature of the eighth aspect of the present invention, it has been experimentally shown that when the working rate is 50% or more, the rigidity value of the body portion is significantly larger than that of the connect portion. Therefore, the rigidity of the body portion is further increased compared to the connect portion.

Consequently, the insertion operability of the catheter guide wire is further improved.

The ninth aspect of the present invention is a method of producing a catheter guide wire which comprises a body portion, a tip end portion and a connect portion for connecting the body portion and the tip end portion, and is seamlessly formed of a material based on Ni and Ti and subjected to a cold working, the method comprising the steps of: subjecting the body portion, the tip end portion and the connect portion to a heat treatment at a temperature of less than 300° C., and after that step subjecting only the connect portion to a heat treatment at a temperature of 300° C. to 350° C.

According to the specified feature of the ninth aspect of the present invention, by subjecting the core wire to plural times of heat treatments, the pushability and operability are further improved. That is, it is possible to realize a catheter guide wire in which the connect portion has higher rigidity rather than super-elasticity, while the connect portion being more flexible than the body portion and maintaining deformation resistance (resistant to permanent deformation).

BRIEF DESCRIPTION OF THE DRAWINGS

Further features and advantages of the present invention will become clear by means of the detailed description made below with reference to the attached drawings, including features and advantages which are not limited to the embodiment.

BEST MODE FOR CARRYING OUT THE INVENTION

In the following, preferred embodiments of the present invention will be described in detail with reference to the attached drawings. The same member will be denoted by the same reference numeral.

Figure 1:
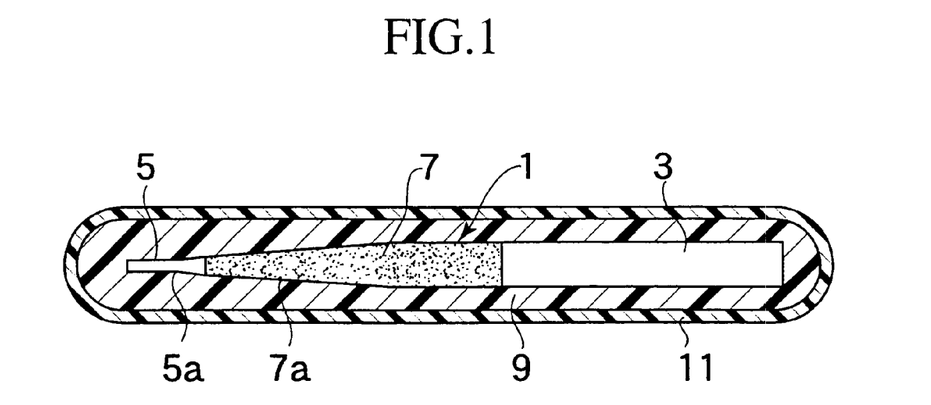
FIG. 1 is a view showing a catheter guide wire coated with a coating resin.

Referring to FIG. 1, a catheter guide wire 1 according to an embodiment of the present invention is used in inserting a catheter into a blood vessel, ureter, trachea or the like, and formed of an identical material composed of Ni—Ti. In this context, the material composed of Ni—Ti is one example of materials based on Ni and Ti, and may be Ni—Ti—X (X is Cu, Co, Fe and V or the like).

The above-mentioned catheter guide wire 1 comprises a body portion 3, a tip end portion 5 having a cross section smaller than that of the body portion 3, and a connect portion 7 for connecting the body portion 3 and the tip end portion 5. Taper portions 7a, 5a are formed from a certain point of the connect portion 7 to a certain point of the tip end portion 5.

In connection with this, the whole length of the catheter guide wire 1 is 450 to 5,000 mm, the tip end portion 5 is 1 to 50 mm long, and the connect portion 7 is 100 to 1,000 mm long. On the other hand, diameters of the body portion 3, the tip end portion 5 and the connect portion 7 are set in the range of 0.3 to 1.0 mm.

On the circumference of the catheter guide wire 1 is coated a coating resin 9 such as polyurethane, in which powder of an X-ray impermeable substance such as bismuth, barium sulfate and tungsten is mixed. Furthermore, the coating resin 9 is coated with a hydrophilic resin 11 such as poly vinyl pyrrolidone.

Figure 2:
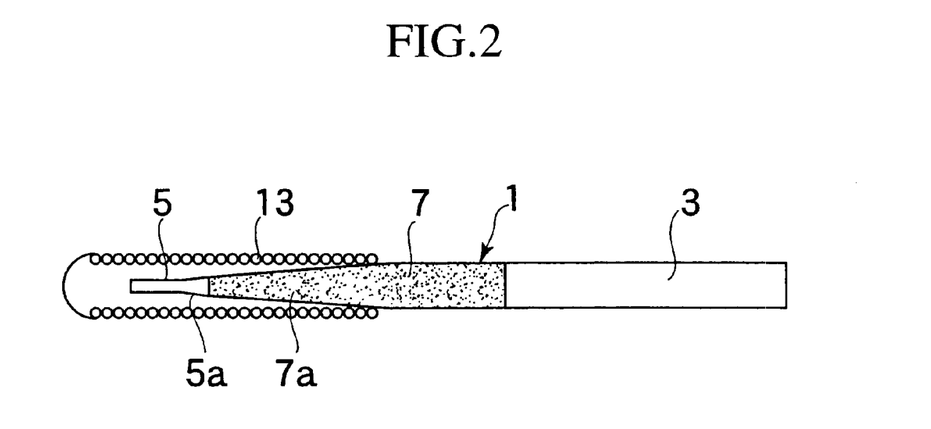
FIG. 2 is a view showing a catheter guide wire to which a metal coil is attached.

In place of coating with the coating resin 9, as shown in FIG. 2, it is also possible to attach a metal coil 13 so as to cover the tip end portion 5 and the taper portion 7a of the connect portion 7, and in that case, a tip end part of the metal coil 13 is formed into a semispherical shape. Incidentally, the metal coil 13 is formed of gold, platinum, silver and the like.

Next, characteristic parts of the embodiment of the present invention will be described.

The body portion 3 and the connect portion 7 are the part that has been subjected to a heat treatment at a temperature of less than 350° C. after cold working at the working rate of 55%, and the connect portion 7 is the part that has been subjected to a heat treatment at a temperature of 400° C. or more (preferably 400° C. to 600° C.) after cold working of 55%.

Figure 3:
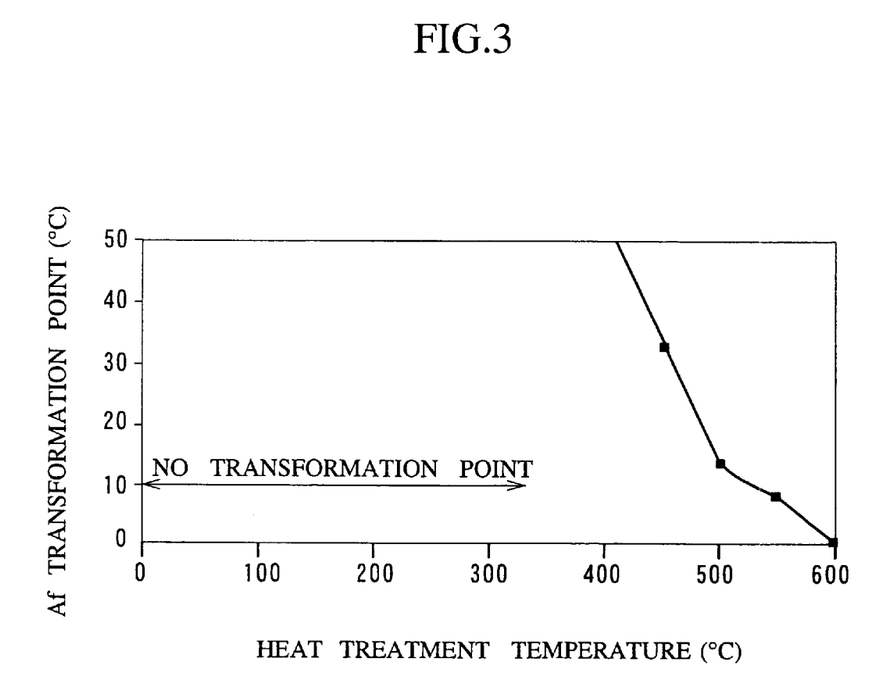
FIG. 3 is a view showing the relationship between heat treatment temperature and transformation point.

Now, it is experimentally shown that in the case where the catheter guide wire 1 formed of Ni—Ti is subjected to a heat treatment, there is such a relationship between heat treatment temperature and transformation point as shown in FIG. 3.

That is, it is experimentally shown that when the catheter guide wire 1 is subjected to a heat treatment at a temperature of less than 350° C., a transformation point will not occur, whereas when the catheter guide wire 1 is subjected to a heat treatment at a temperature of 400° C. or more (preferably 400° C. to 600° C.), a transformation point will occur. Therefore, the body portion 3 and the tip end portion 5 are the parts that do not have a transformation point. On the other hand, the connect portion 7 is the part that has a transformation point (according to the present embodiment, it is preferred to set the transformation point at about 34° C. which is slightly lower than the body temperature), and hence is able to cause stress-inducible martensite transformation and its reverse transformation.

In the drawing, the part having a transformation point in the catheter guide wire 1 is distinguished from the part not having a transformation point by giving a scattered-dot pattern consisting of a plurality of dots.

Figure 4:
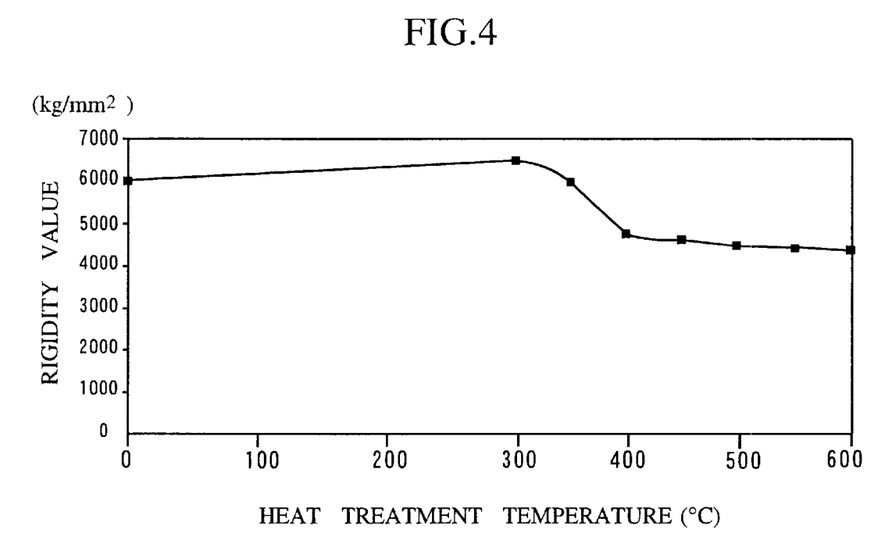
FIG. 4 is a view showing the relationship between heat treatment temperature and rigidity value.
Figure 5:
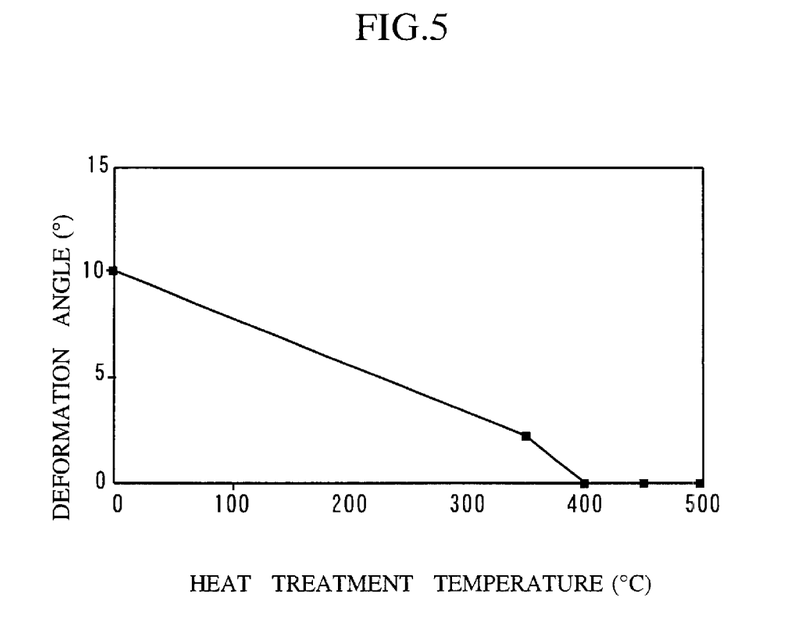
FIG. 5 is a view showing the relationship between heat treatment temperature and deformation angle.

Furthermore, it is experimentally shown that in the case where the catheter guide wire 1 is subjected to a heat treatment, there is a relationship between heat treatment temperature and rigidity value as shown in FIG. 4, and there is a relationship between heat treatment temperature and deformation angle as shown in FIG. 5.

That is, it is experimentally shown that when the catheter guide wire 1 is subjected to a heat treatment at a temperature of less than 350° C., a the rigidity value will become large, whereas when the catheter guide wire 1 is subjected to a heat treatment at a temperature of 400°C. or more (preferably 400° C. to 600° C.), it will super-elastically deform.

In this context, the term "rigidity value" represents the degree of strength against bending rather than the degree of strength against tensile.

Figure 6:
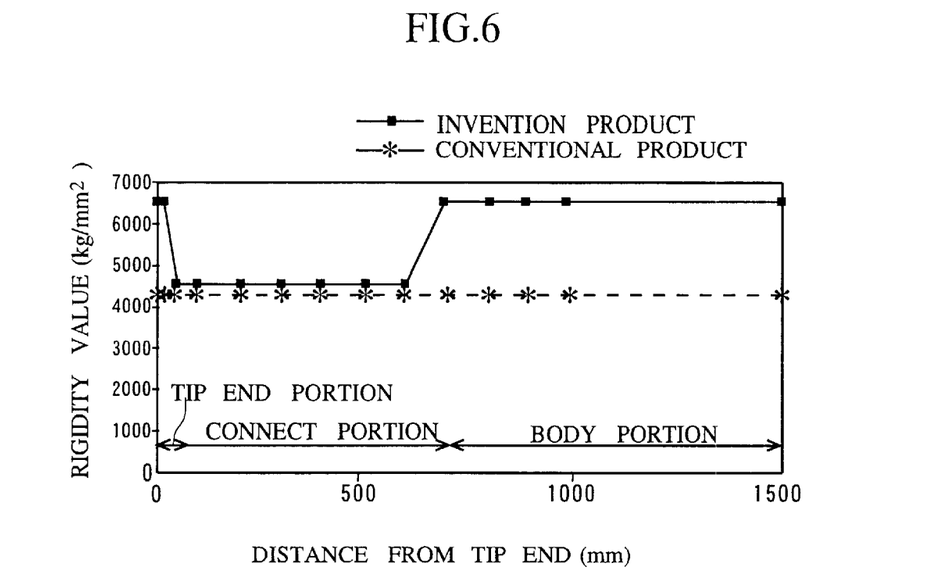
FIG. 6 is a view showing the relationship between distance from the tip end of the catheter guide wire and rigidity value.
Figure 7:
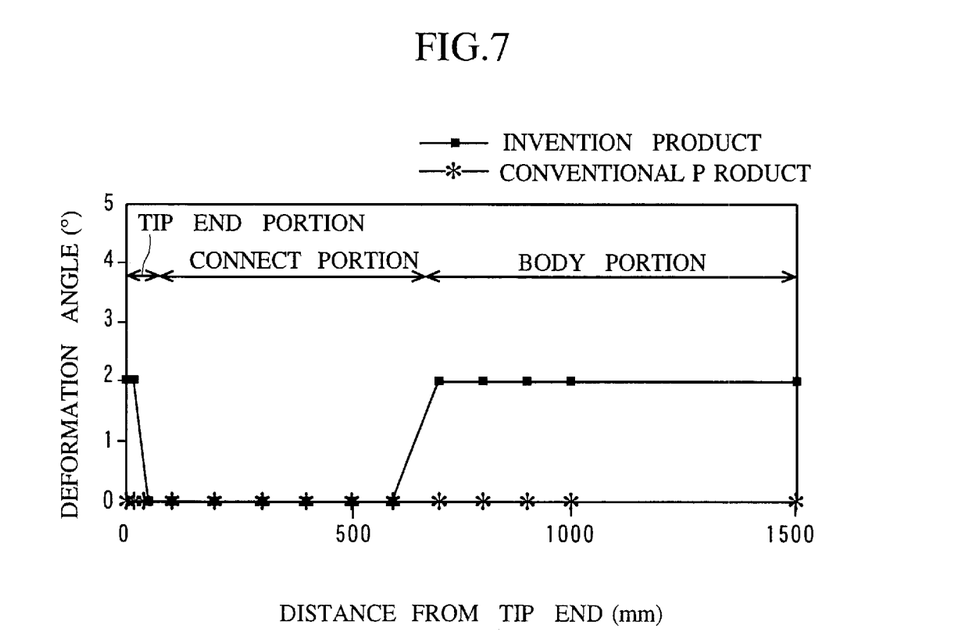
FIG. 7 is a view showing the relationship between distance from the tip end of the catheter guide wire and deformation angle.
Figure 8:
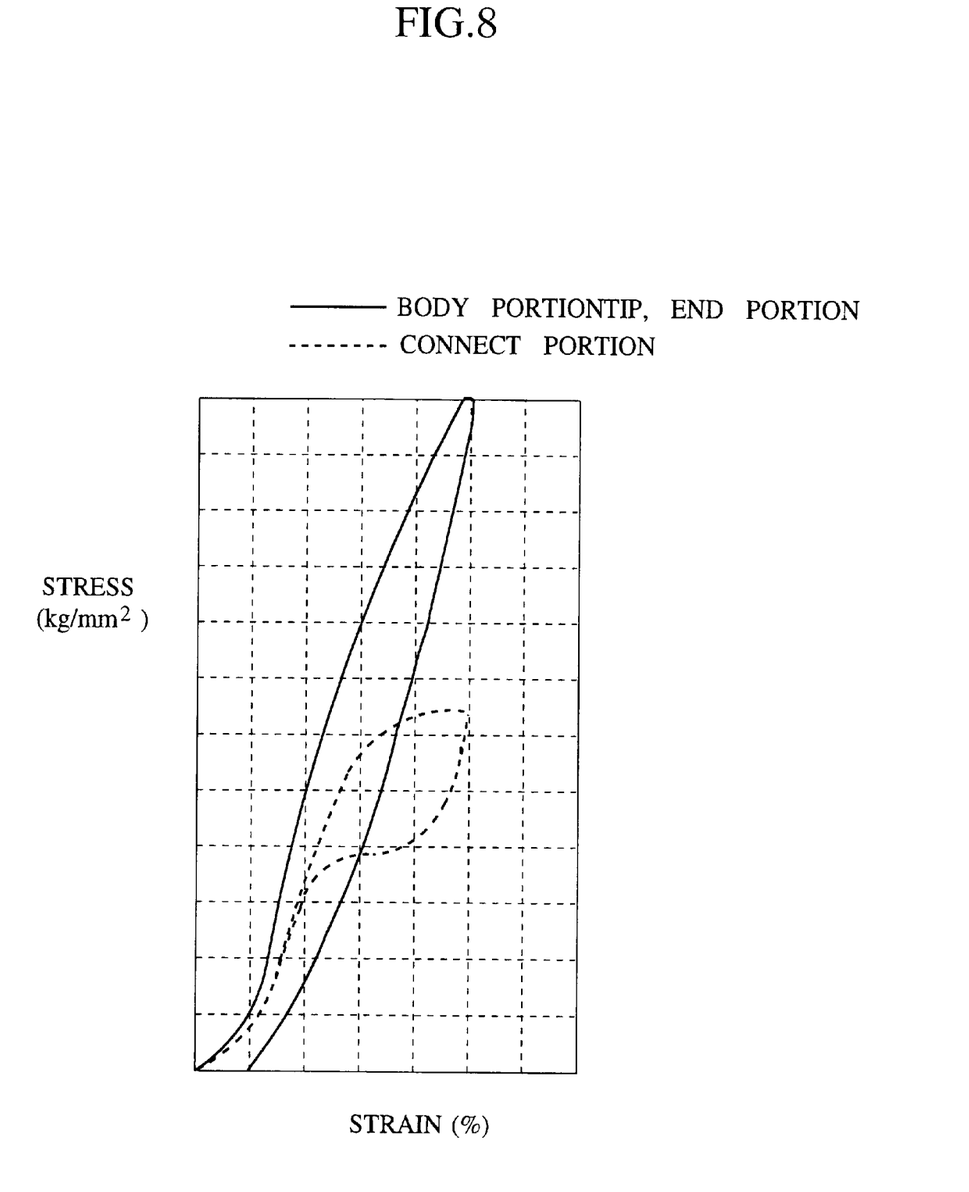
FIG. 8 is a view showing the relationship between strain and stress at each portion of the catheter guide wire.

Furthermore, in the case where the body portion 3 and the tip end portion 5 are subjected to a heat treatment at a temperature of 300° C. for 50 seconds, and the connect portion 7 is subjected to a heat treatment at a temperature of 450° C. for 5 minutes, the relationship between distance from the tip end of the catheter guide wire 1 and rigidity value, the relationship between distance from the tip end and deformation angle, and the relationship between strain and stress are shown in FIGS. 6, 7 and 8, respectively. Incidentally, FIGS. 6 and 7 also show the above-mentioned relationships for a conventional catheter wire in which each portion has a transformation point as a comparative example.

Therefore, the body portion 3 is the part not having a transformation point, so that it will not super-elastically deform and hence has appropriate rigidity without becoming excessively flexible. Similarly, the tip end portion 5 is the part not having a transformation point, so that it will not super-elastically deform but can be plastically deformed. Furthermore, the connect portion 7 is the part having a transformation point, so that it can super-elastically deform via stress-inducible martensite transformation and its reverse transformation, and has flexibility (softness).

Figure 9:
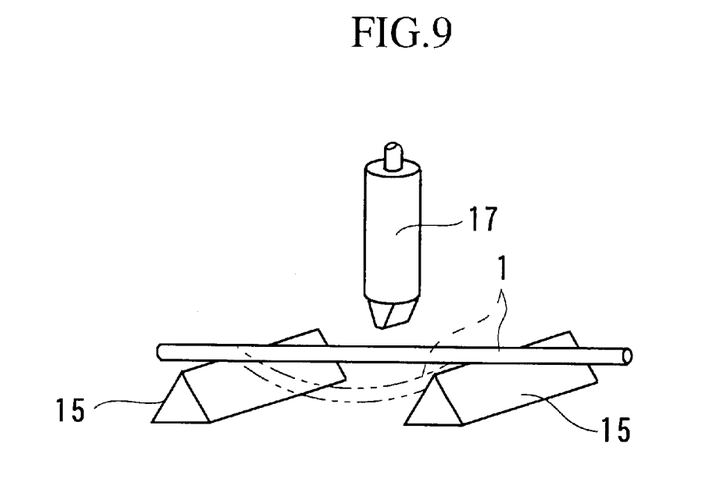
FIG. 9 is a view schematically showing the content of the experiment for determining rigidity value.
Figure 10A:
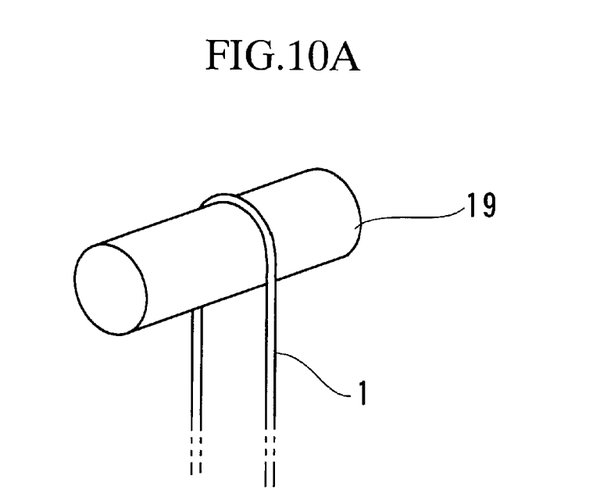
FIGS. 10A and 10B are views schematically showing the content of the experiment for determining deformation angle.
Figure 10B:
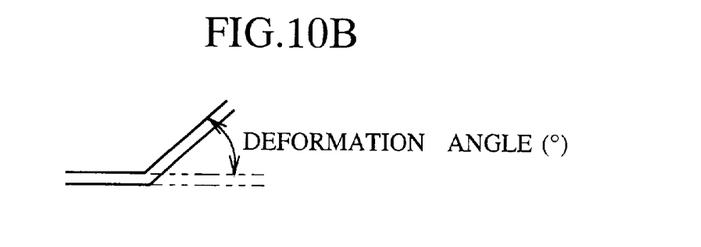

Incidentally, rigidity value can be determined, in the situation that the catheter guide wire 1 is bend-deformed by pressing a pressing member 17 of a press machine by 3 mm from upward at the midpoint between fulcrums of the catheter guide wire 1 which is supported on a pair of supporting members 15 having a fulcrum-fulcrum distance of 15 cm as shown in FIG. 9, on the basis of the bending load of the pressing member 17. On the other hand, deformation angle refers to a deformation angle as shown in FIG. 10B in the case where the catheter guide wire 1 which has been wound on a winding member 19 having a diameter of 15 mm for 30 seconds, as shown in FIG. 10A, is released from the wound condition.

Figure 11:
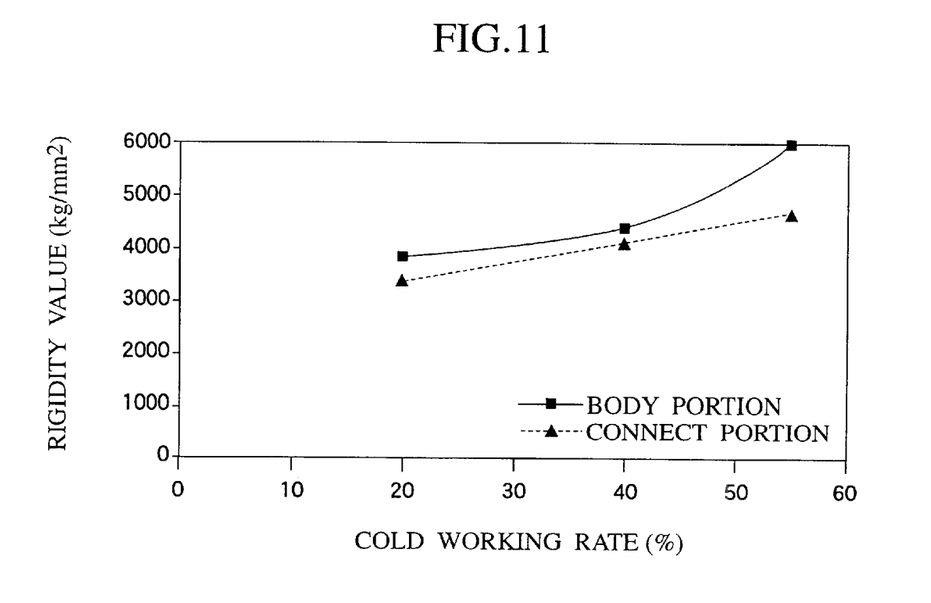
FIG. 11 is a view showing the relationship between working rate of cold working and rigidity value.

Furthermore, it is experimentally shown that in the case where the body portion 3 and the connect portion 7 in the catheter guide wire 1 are subjected to a heat treatment (heat treatment at a temperature of 350° C. for 1 minute or less for the body portion 3, and heat treatment at a temperature of 450° C. for 1 minute or more for the connect portion 7), there is such a relationship between cold working rate and rigidity value as shown in FIG. 11.

That is, it is experimentally shown that when the working rate of the cold working is 50% or more, the rigidity value of the body portion 3 becomes significantly larger than that of the connect portion 7. Therefore, if the working rate of the cold working is 50% or more, the rigidity of the body portion 3 is further increased compared to the connect portion 7.

Now, in order to make the above-mentioned operation sufficiently effective in the catheter guide wire 1 the rigidity values of the body portion 3 and the tip end portion 5 are 5,500 to 7,000 Kg/mm$^2$, and the rigidity value of the connect portion 7 is 3,500 to 5,000 Kg/mm$^2$.

Next, a method of producing the catheter guide wire 1 will be described including the operation thereof.

An identical material of Ni—Ti is subjected to a cold working at a working rate of 55%, to be formed into a desired shape, thereafter the whole guide wire 1 is subjected to a heat treatment at a temperature of less than 350° C. for 30 seconds or more. Then the connect portion 7 is subjected to a heat treatment at a temperature of 400° C. or more (preferably 400° C. to 600° C.) for 1 minute or more.

Consequently, as described above, the body portion 3 is the part not having a transformation point, so that it will not super-elastically deform and hence can have appropriate rigidity without becoming excessively flexible. Similarly, the tip end portion 5 is the part not having a transformation point, so that it will not super-elastically deform but can be plastically deformed. Furthermore, the connect portion 7 is the part having a transformation point, so that it can super-elastically deform via stress-inducible martensite transformation and its reverse transformation, and has flexibility (softness).

As described above, according to the present embodiment of the present invention, since the body portion 3 will not become excessively flexible and has appropriate rigidity, while the connect portion 7 has flexibility, the power of pressing the catheter guide wire 1 is sufficiently transmitted to the connect portion 7 side from the body portion 3 side, so that the insertion operability of the catheter guide wire 1 is improved. In particular, since the working rate of the cold working is 55%, the rigidity is further improved in the body portion 3 compared to the connect portion 7, so that the insertion operability of the catheter guide wire is further improved.

In addition, since the tip end portion 5 can be plastically deformed, a physician can shape the tip end portion 5 into an appropriate shape in accordance with the situation during operation.

Figure 12:
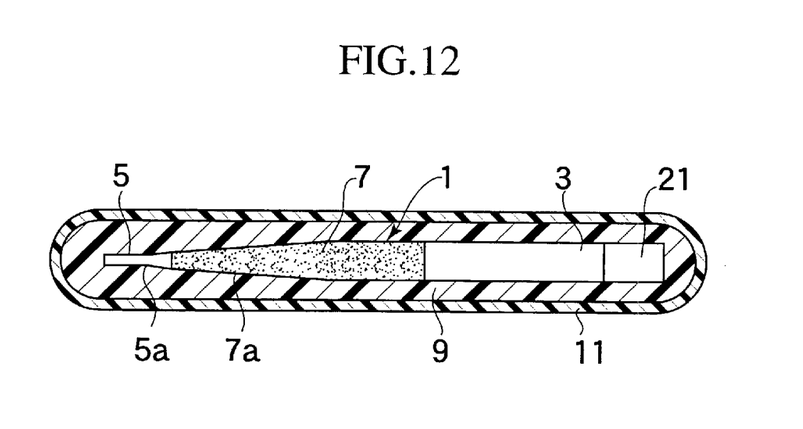
FIG. 12 is a view showing another embodiment of the catheter guide wire.

Incidentally, in the present embodiment of the present invention, in addition to the body portion 3, the tip end portion 5 and connect portion 7, the catheter guide wire 1 may have an additional member 21 not having a transformation point shown as the second embodiment in FIG. 12.

Next, a catheter guide wire in which the above-mentioned guide wire is further improved will be described as the third embodiment.

In the case of a working effective type Ni—Ti alloy, there is an inversely proportional relationship between rigidity value and permanent deformation amount, i.e., deformation angle of plastic deformation. Furthermore, the property that is required for a core wire of the guide wire is that it has a portion having high rigidity, and a portion that does not deform when the guide wire is inserted into a highly bent part. The portion that does not deform is not required for the whole length of the core wire of the guide wire. The reason is that the location of the guide wire inserted into a highly bent blood vessel is nearly fixed regardless of the case of disease. Furthermore, since the tip end portion 5 is low in bending stress and hence excellent in deformation resistance because of small diameter of a wire (thin wire) due to the taper working, it is the connect portion 7 that has to have deformation resistance.

From the above, it is necessary to make improvement into a catheter guide wire having both a portion of a single core wire having high rigidity, and a portion which has comparatively high rigidity and excellent deformation resistance. In the present invention, such an improved catheter guide wire could be achieved by subjecting the core wire to multiple heat treatments. As a result of this, the improvement was made to provide a catheter guide wire which is excellent in pushability and operability compared to the catheter guide wire of the above-mentioned embodiment. That is, it was possible to realize a catheter guide wire in which the connect portion 7 has higher rigidity rather than super-elasticity, while the connect portion 7 being more flexible than the body portion 3 and maintaining deformation resistance (resistant to permanent deformation).

In the following, the third embodiment of the improved catheter guide wire as described above will be described in detail. The same part as in the drawings of the preceding embodiments will be explained by referring to the drawing of the first embodiment.

In this embodiment, the whole length of the catheter guide wire 1 is 1,500 mm, for example, the tip end portion 5 is 50 to 200 mm long, the connect portion 7 is 50 to 800 mm long. On the other hand diameters of the body portion 3, the tip end portion 5 and the connect portion 7 are set in the range of 0.3 to 1.0 mm. The condition of the hydrophilic resin 11 of the coating resin 9 is as same as that of the first embodiment.

The above-mentioned catheter wire 1 is produced in such a way that after subjecting the body portion 3, the tip end portion 5 and the connect portion 7 to a cold working at the working rate of 55%, the portions are subjected to a heat treatment at a temperature of less than 300° C. for reforming, thereafter only the connect portion 7 is subjected to a heat treatment at a temperature of not less than 300° C. and less than 350° C.

In other words, after forming the identical method of Ni—Ti into a desired shape by performing the cold working at the working rate of 55%, first the whole guide wire 1 is subjected to a heat treatment at a temperature of less than 300° C. for 30 seconds or more. Then only the connect portion 7 is subjected to a heart treatment at a temperature of 300° C. to 350° C. for 1 minute or more. Consequently, the connect portion 7 does not have super-elasticity.

As a result of the above working, the rigidity of the above-mentioned catheter guide wire 1 is 7,000 for the tip end portion 5, 5,000 to 6,000 (desirably 5,500) for the connect portion 7, and 6,500 or more (desirably 7,000) for the body portion 3. Furthermore, the deformation angle (permanent deformation amount) is 18 degrees for the tip end portion 5, 3 degrees for the connect portion 7 and 18 degrees for the body portion 3.

Incidentally, deformation angle refers to a deformation angle as shown in FIG. 10B in the case where the catheter guide wire 1 which has been wound on a winding member 19 having a diameter of 6 mm for 30 seconds at 180 degrees, as shown in FIG. 10A, is released from the wound condition.

According to the production method as described above, the catheter guide wire 1 according to the third embodiment was improved to have more excellent pushability and operability by subjecting the core wire to multiple heat treatments. That is, it was possible to realize a catheter guide wire in which the connect portion 7 has higher rigidity rather than super-elasticity, while the connect portion 7 being more flexible than the body portion 3 and maintaining deformation resistance (resistant to permanent deformation).

While a preferred embodiment of the invention has been described using specific terms, such description is for illustrative purpose only, and it is to be understood that changes and variations may be made without departing from the spirit or scope of the following claims.

INDUSTRIAL APPLICABILITY

As described above, a method of producing a catheter guide wire and a catheter guide wire produced by such a method according to the present invention are applicable to a catheter guide wire which is used in inserting a catheter into a blood vessel, ureter, trachea or the like, or to use in inserting a guide wire into a blood vessel or the like in conformance with the shape of the blood vessel or the like.

What is claimed is:

1. A catheter guide wire comprising:

a body portion;

a tip end portion having a cross section that is smaller than a cross section of said body portion; and a connect portion for connecting the body portion and the tip end portion, the connect portion being formed with a taper portion, wherein the body portion, the tip end portion and the connect portion are searnlessly formed of an identical material;

the body portion and the tip end portion not having a transformation point, and wherein the tip end portion can be plastically deformed; and the connect portion having a transformation point and wherein the connect portion can be super-elastically deformed.

2. The catheter guide wire according to claim 1, wherein the identical material is based on Ni and Ti;

the body portion and the tip end portion not having a transformation point are heat treated at a temperature of less than 350° C. after cold working; and the connect portion having a transformation point is heat treated at a temperature of more than or equal to 400° C. after cold working.

3. A catheter guide wire comprising:

a body portion;

a tip end portion having a cross section smaller than a cross section of the body portion wherein the tip end portion can be plastically deformed; and a connect portion for connecting the body portion and the tip end portion, the connect portion being formed with a taper portion, wherein the guide wire is seamlessly formed of a material based on Ni and Ti;

the body portion has a rigidity value of 5,500 to 7,000 Kg/mm$^2$; and the connect portion has a rigidity value of 3,500 to 5,000 Kg/mm$^2$.

4. A catheter guide wire comprising;

a body portion;

a tip end portion having a cross section smaller than a cross section of the body portion wherein the tip end portion can be plastically deformed; and a connect portion for connecting the body portion and the tip end portion, the connect portion being formed with a taper portion, wherein, the guide wire is seamlessly formed of a material based on Ni and Ti;

the body portion has a rigidity value of 6,500 Kg/mm$^2$ or more; and the connection portion has a rigidity value of 5,000 to 6,000 Kg/mm$^2$.

5. A method of producing a catheter guide wire which comprises a body portion, a tip end portion, and a connect portion for connecting the body portion and the tip end portion, and is seamlessly formed of a material based on Ni and Ti and subjected to a cold working, the method comprising the steps of:

subjecting the body portion and the tip end portion to a heat treatment at a temperature of less than 350° C. wherein said tip end portion is plastically deformable; and subjecting the connect portion to a heat treatment at a temperature of 400° C. or more wherein said connect portion is super-elastically deformable.

6. The method of producing a catheter guide wire according to claim 5, wherein the working rate of the cold working is 50% or more.

7. A method of producing a catheter guide wire which comprises a body portion, a tip end portion, and a connect portion for connecting the body portion and the tip end portion, and is seamlessly formed of a material based on Ni and Ti and subjected to a cold working, the method comprising the steps of:

subjecting the body portion, the tip end portion and the connect portion to a heat treatment at a temperature of less than 300° C., wherein the tip end portion is plastically deformable; and after the above heat treatment, subjecting only the connect portion to a heat treatment at a temperature of 300° C. to 350° C.

8. The method of producing a catheter guide wire according to claim 7, wherein the working rate of the cold working is 50% or more.

* * * * *